United States Patent [19]
Rosado

[11] 4,171,754
[45] Oct. 23, 1979

[54] SCENTING OR PERFUMING LAMP
[76] Inventor: Ruperto L. Rosado, 2644 Beaumont St., Sacramento, Calif. 95815
[21] Appl. No.: 789,269
[22] Filed: Apr. 20, 1977
[51] Int. Cl.² .............................................. B67D 5/08
[52] U.S. Cl. ...................................... 222/70; 222/76; 222/78; 222/113; 362/122
[58] Field of Search ................... 222/70, 113, 78, 76; 362/122, 101; 239/211

[56] References Cited
U.S. PATENT DOCUMENTS

| | | | |
|---|---|---|---|
| 1,701,032 | 2/1929 | Dubray | 239/211 |
| 3,187,949 | 6/1965 | Mangel | 222/70 |
| 3,351,240 | 11/1967 | Gray | 222/70 |
| 3,627,176 | 12/1971 | Sailors | 222/70 |
| 3,848,775 | 11/1974 | Possell | 222/70 |

FOREIGN PATENT DOCUMENTS 33408 10/1964 German Democratic Rep. ..... 362/122

Primary Examiner—Robert J. Spar
Assistant Examiner—Charles A. Marmor
Attorney, Agent, or Firm—Blair, Brown & Kreten

[57] ABSTRACT

A simulated potted plant including one or more artificial flowers having tubular stems extending from a vase, each flower provided with a socket for an illuminating lamp bulb and a pressurized source of scenting fluid together with an electrical timer in the vase for automatically dispensing the scenting fluid through the stem and from the flower at a selected interval and duration with the lamp bulb and timer energized by an associated source of electrical power.

4 Claims, 8 Drawing Figures

MONOSTABLE MULTIVIBRATOR

RELAXATION OSCILLATOR

SCENTING OR PERFUMING LAMP

BACKGROUND OF THE INVENTION

FIELD OF THE INVENTION

The following invention relates generally to an illuminated scented floral structure whose flowers comprise a socket for the light bulbs disposed thereon, and also provides the outlet tube for dispensing a fragrance into the air.

SUMMARY OF THE INVENTION

The problem with most potted plants is that they can only be truly enjoyed a portion of the year. This is because they bloom infrequently and only seasonally. With the following invention a plant is provided which appears to be in bloom year round, and also provides the observer with a sweet smell or scent, as well as illumination. Automatic timing means are provided to regulate the dispersion of the fragrance.

Accordingly it is an object of this invention to provide a simulated floral device which is illuminated.

It is another object of this invention to provide a floral device which is also scented.

It is a further object of this invention to provide a floral arrangement in which the scenting is done automatically.

These and other objects of the following invention will become more clear when considering the appended drawings and following detailed specification.

DESCRIPTION OF THE PREFERRED EMBODIMENT

Figure 1:
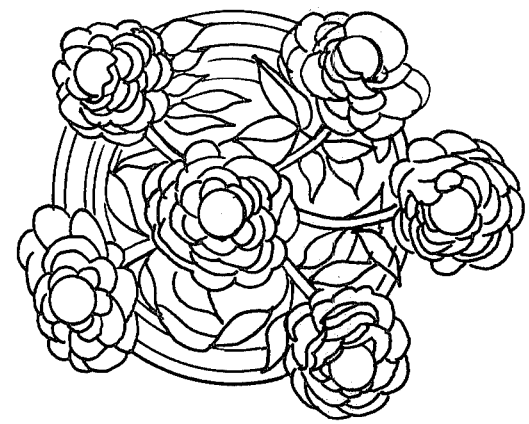
FIG. 1 shows a top view of the floral arrangement.
Figure 2:
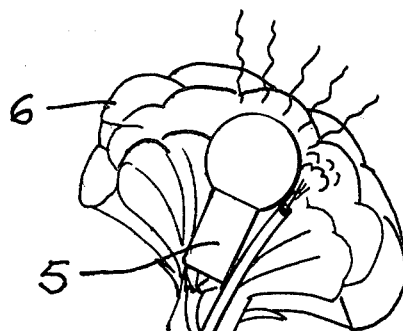
FIG. 2 shows a side view of the floral arrangement.
Figure 2:
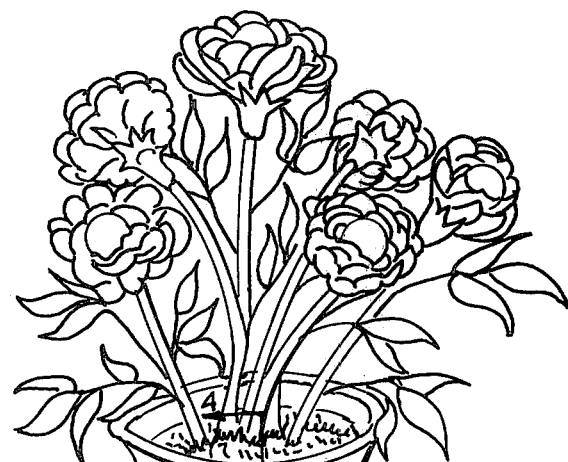
Figure 3:
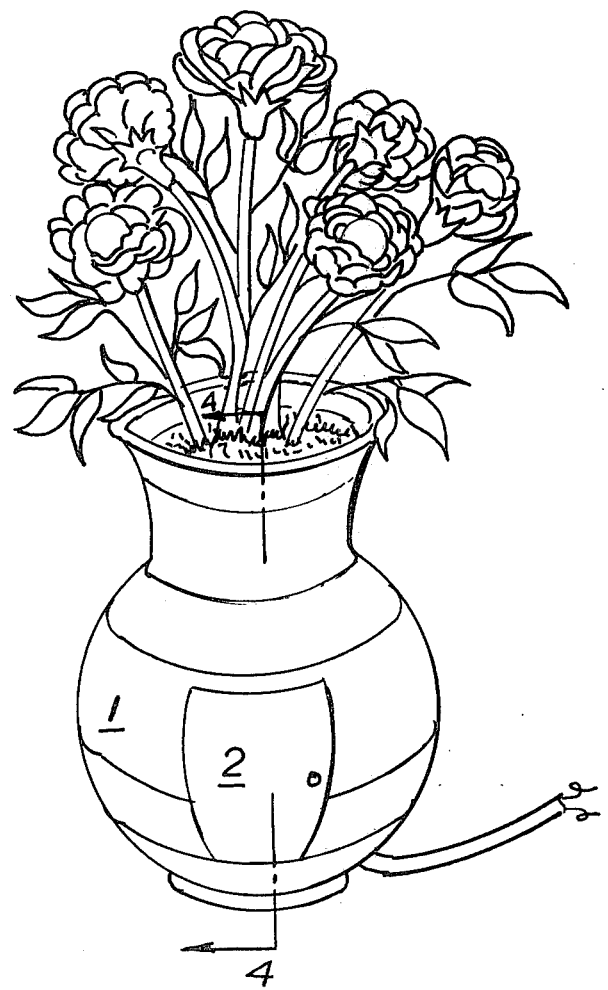
FIG. 3 shows a depiction of one flower of the floral arrangement showing the illuminating means as well as the scenting means.
Figure 3:
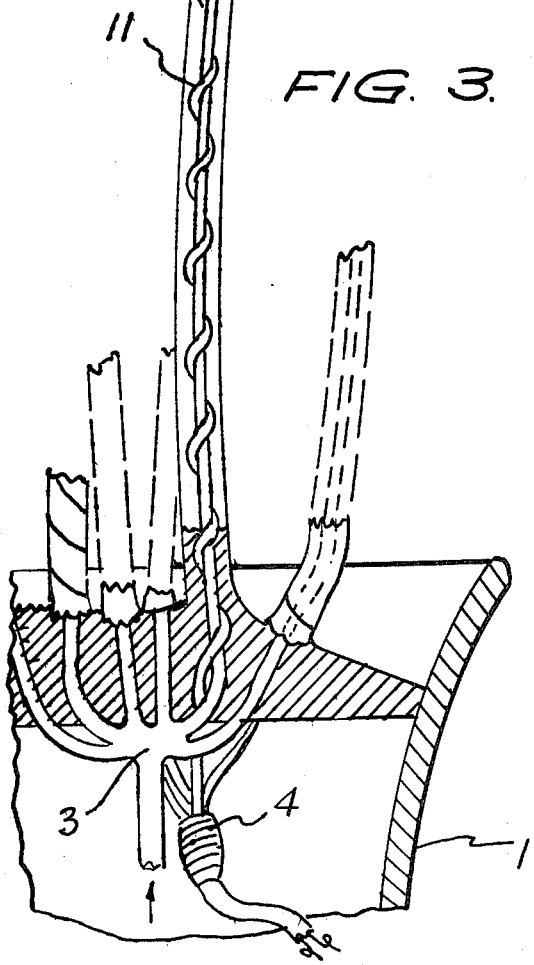

Turning to FIGS. 1 through 3 now it will be seen that vase 1 has a door 2 disposed thereon. Emanating from vase 1 is a floral arrangement comprised of a plurality of floral heads 6, having illuminating means 5 disposed therein, and a scenting tube 3 best seen in FIG. 3. Lamp 5 is connected to a power source not shown through wiring 4 which wraps around the scenting tube 3 in the interior portion of the stem 11.

Figure 4:
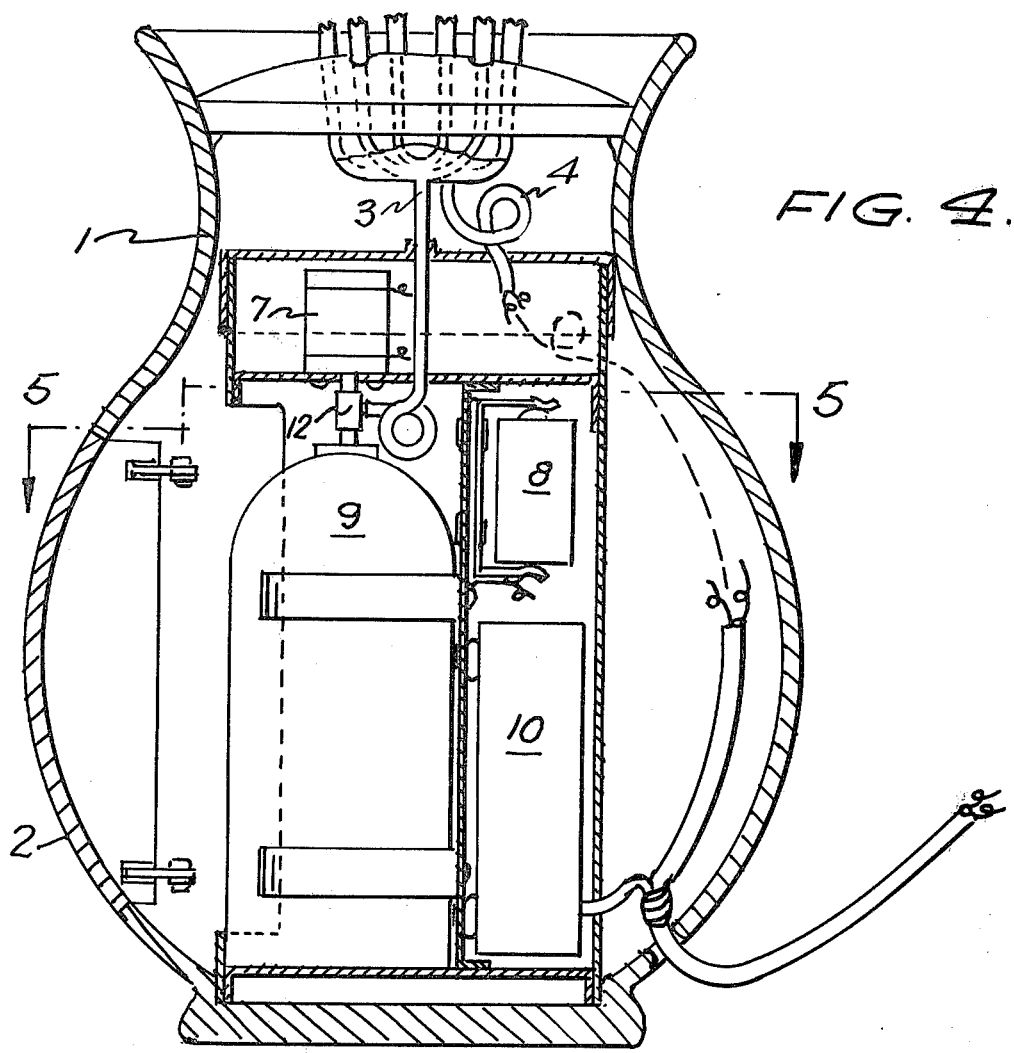
FIG. 4 is a sectional view taken along the line 4—4 of FIG. 2.
Figure 5:
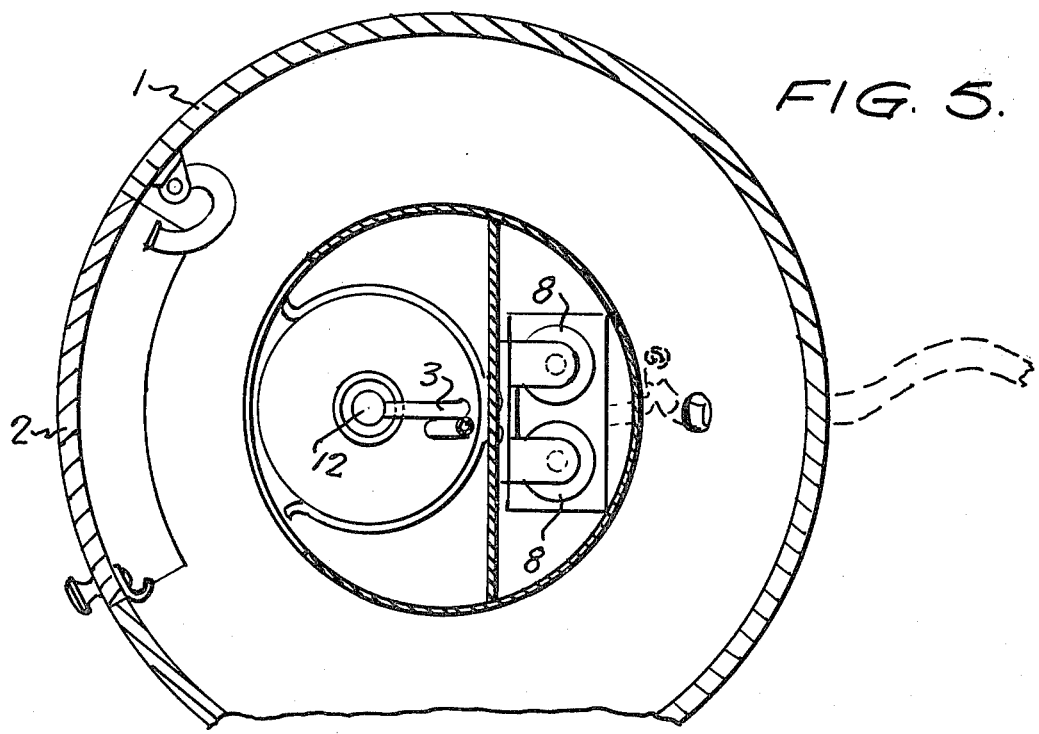
FIG. 5 is a sectional view taken along the line 5—5 of FIG. 4.

The scenting tube 3 extends from a pressurized container 9 in which the perfume or disinfectant, may be disposed. Dispersion of the liquid contained in container 9 is controlled and regulated through solenoid 7 located above the container and serves as a valve actuator. This is best depicted in FIGS. 4 and 5. Also shown there is the power source which in one embodiment may be a battery member 8, or the control circuitry designated by 10 in FIG. 4 and better seen in FIGS. 6, 7 and 8.

Figure 8:
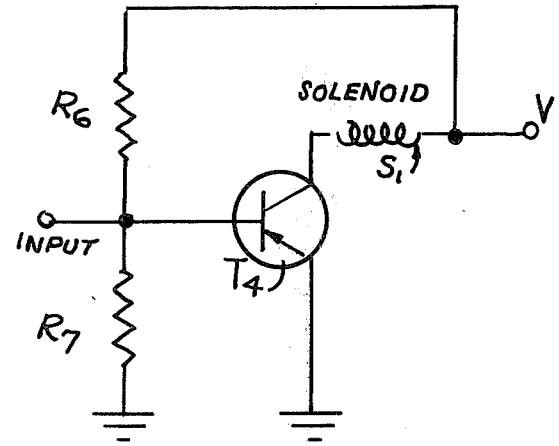
FIG. 8 shows the actuating mechanism for the valve means of the floral arrangement seen in FIGS. 4 and 5.

FIG. 8 shows the actuation of the solenoid S1 delineated therein and corresponding to numeral 7 of FIG. 4. It will be noted that transistor element T4 cooperates with S1 and resistors R6 and R7 to provide the actuation of the solenoid and therefore the valve member disposed below solenoid 7 seen in FIG. 4. The valve is located at 12 in FIG. 4.

Figure 7:
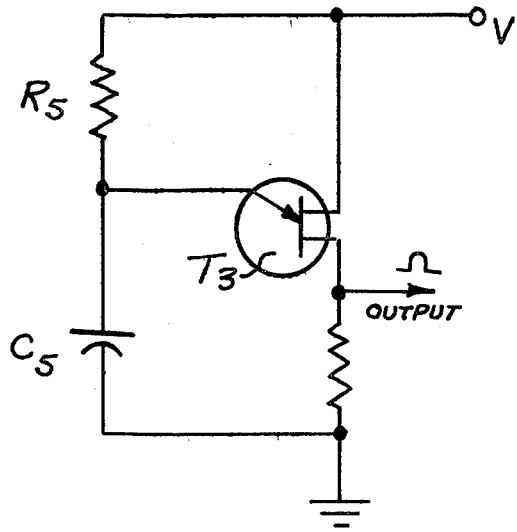
FIG. 7 shows a relaxation oscillator which starts the circuit in FIG. 6.

FIG. 7 shows the details of the relaxation oscillator which in this case serves to turn on the scenting as will be described hereinbelow. Transistor T3 is preferably a unipolar transistor and cooperates with resistor R5 and capacitor C5 to provided a timing operation for determining when the circuitry for providing the scenting mechanism should be actuated.

By appropriately selecting the values of R5 and C5 the time lag for when the scenting circuitry is on can be infinitely varied. In essence however the value of C5 reaches a certain point when the gate in the unipolar transistor T3 opens and provides a voltage output which is to be delivered to the input segment of monostable multivibrator shown in FIG. 6. The output of the relaxation oscillator is connected to a coupling capacitor C4 of FIG. 6 and serves to actuate transistor element T1 in much the same way that transistor element T3 was actuated in FIG. 7.

That is transistor element T1 cooperates with resistors R1, R2, R3 and R4 etc. in conjunction with the values selected for capacitors C1 to provide a gate situation as shown in FIG. 7, T3. When the voltage has reached a certain level over capacitor C1 transistor element T1 will open and provide current to the second half of the multivibrator circuit.

There transistor element T2 is similarly affected and the duration of that transistor element T2 will remain in its actuated state depending on the capacitors associated in that segment of the circuit as well as the specific value for capacitors C2 and C3.

Figure 6:
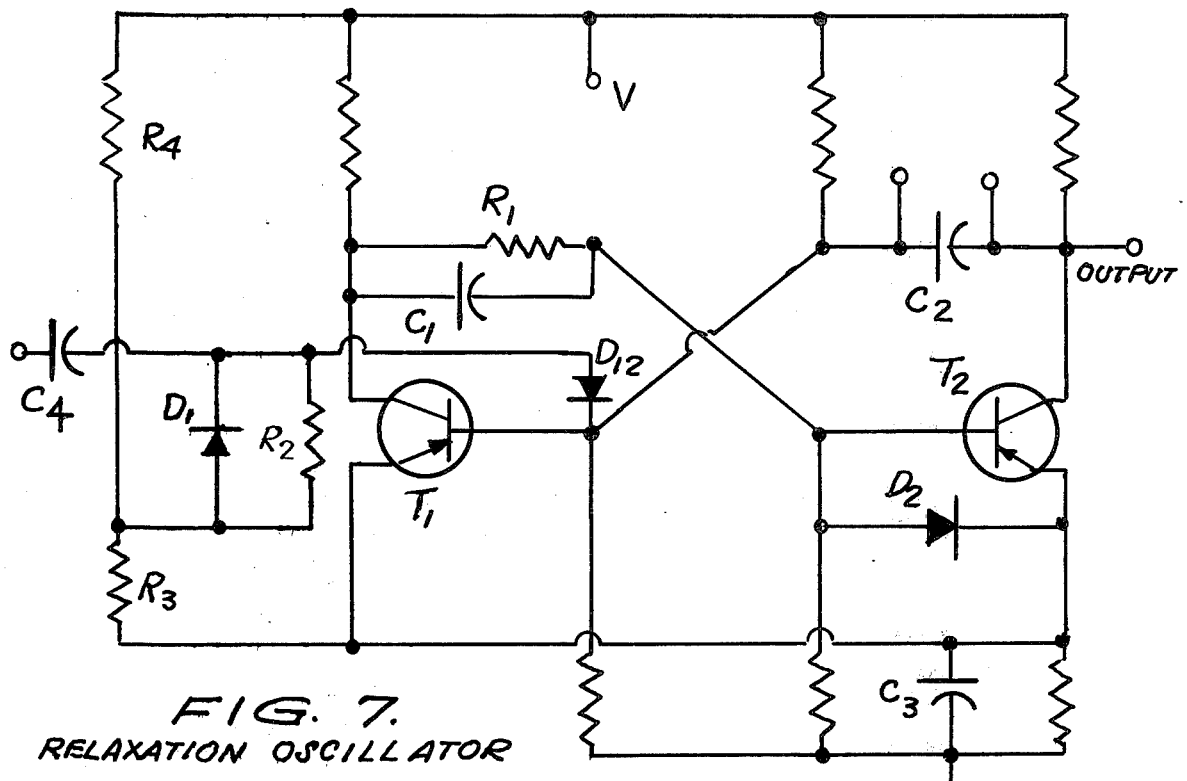
FIG. 6 shows the circuitry for actuation of the fragrance dispersing mechanism.

The net affect of the two transistors located in FIG. 6 is the T1 will turn on the circuit for example to start spraying action and T2 will terminate this function so as to turn it off. The output of FIG. 6 constitutes the input used in FIG. 8. That is when electricity is being provided from the output of FIG. 6 the solenoid is working in FIG. 8 thereby providing a scent being disposed in the room. The values of all of the capacitors and resistors in the three circuits determine the amount of time that the circuit will remain in its off position and also the amount of time the circuit will remain in its on position.

In operation then it will be seen that electrical stimulation of the circuitry shown in FIGS. 6, 7 and 8 and generally depicted by numeral 10 in FIG. 4 will provide actuation of the valve which is designated by numeral 12. This valve is controlled by solenoid 7 and its actuation release the contents of preferably perfume contained in container number 9. After the valve is open, the perfume goes through network 3 and up the stems of the flowers to be distributed into the room. Battery 8 provides an alternative form of power for the circuitry. The light shown in FIG. 3 is actuated by the wiring 4 which extends to a conventional outlet, or maybe connected directly to the battery.

Having thus described the preferred embodiment of the invention it should be understood that numerous structural modifications and adaptations may be resorted to without departing from the spirit of the invention.

What is claimed is:

1. A scenting lamp comprising, in combination, a vase, a floral arrangement in said vase including at least one floral head having a stem, illuminating means disposed within said floral head, an associated source of electrical power for energizing said illuminating means, a container of pressurized scenting fluid having an outlet supported on said vase, valve means operatively associated with said container, conduit means extending within said stem and having an outlet end within said floral head for conducting said pressurized scenting fluid to said floral head, means for controlling said valve means to periodically spray said scenting fluid from said conduit means outlet end, said controlling means comprising electrical timing means for automatically actuating said valve means to spray said scenting fluid from said outlet end at predetermined intervals and for a predetermined duration, said electrical timing means including a solenoid for actuating said valve means, a monostable multivibrator having an output connected to said solenoid for energizing said solenoid for a predetermined period of time, a relaxation oscillator having an output connected to the input of said monostable multivibrator for actuating said monostable multivibrator at predetermined intervals of time and a source of electrical power connected to said solenoid, said monostable multivibrator and said relaxation oscillator.

2. A scenting lamp in accordance with claim 1 wherein said source of power for said illuminating means comprises a battery.

3. A scenting lamp comprising, in combination, a vase, a floral arrangement in said vase including at least one floral head having a stem, illuminating means disposed within said floral head, an associated source of electrical power for energizing said illuminating means, a container of pressurized scenting fluid having an outlet supported on said vase, valve means operatively associated with said container, conduit means extending within said stem and having an outlet end within said floral head for conducting said pressurized scenting fluid to said floral head, means for controlling said valve means to periodically spray said scenting fluid from said conduit means outlet end, said controlling means comprising electrical timing means for automatically actuating said valve means to spray said scenting fluid from said outlet end at predetermined intervals and for a predetermined duration, said electrical timing means including a solenoid for actuating said valve means, a source of electrical power connected to one side of said solenoid, a transistor having its collector connected to the other side of said solenoid, and a timing circuit having an output coupled to the base of said transistor whereby said solenoid is energized when said transistor is turned on by the output from said timing circuit for actuation of said valve means wherein said timing circuit includes a monostable multivibrator having an input, a source of power connected to said multivibrator, said multivibrator including a pair of transistors, a plurality of resistors connected to said transistors, the base of each of said transistors connected through a capacitor to the collector of the other of said transistors, said multivibrator having an output forming said timing circuit output to feed a voltage pulse having a duration determined by the valves of said capacitors and said resistors to the base of said transistor connected to said solenoid and means coupled to the input of said multivibrator for providing a triggering voltage signal at predetermined intervals.

4. A scenting lamp in accordance with claim 3 wherein said means for providing said triggering voltage signal comprises a relaxation oscillator including a unijunction transistor and a RC network connected to the emitter of said unijunction transistor, a source of power connected to one base of said unijunction transistor and an output connected to the other base of said unijunction transistor, means for coupling the output of said unijunction transistor to the input of said multivibrator, the resistor and capacitor of said RC network having selected values for turning on said unijunction transistor at a selected frequency to provide said triggering voltage signal for said multivibrator at said predetermined intervals.

* * * * *